(12) United States Patent
Yerbic

(10) Patent No.: US 8,143,053 B2
(45) Date of Patent: Mar. 27, 2012

(54) LOCKABLE CELL GROWTH CHAMBER WITH ANTILOCKING FEATURE

(75) Inventor: Patrick Yerbic, St. Louis, MO (US)

(73) Assignee: Biomerieux, Inc., Hazelwood, MO (US)

( * ) Notice: Subject to any disclaimer, the term of this patent is extended or adjusted under 35 U.S.C. 154(b) by 362 days.

(21) Appl. No.: 12/589,777

(22) Filed: Oct. 26, 2009

(65) Prior Publication Data

US 2011/0097790 A1 Apr. 28, 2011

(51) Int. Cl.
*C12M 1/22* (2006.01)
(52) U.S. Cl. .................. 435/305.3; 435/297.5
(58) Field of Classification Search .............. 435/288.3, 435/297.5, 305.1, 305.4; 215/44; 141/103; 220/300, 302, 784
See application file for complete search history.

(56) References Cited

U.S. PATENT DOCUMENTS

| | | | |
|---|---|---|---|
| 3,769,936 A | 11/1973 | Swanson et al. |
| D238,886 S | 2/1976 | Goy |
| 4,988,302 A | 1/1991 | Smith et al. |
| 5,638,976 A | 6/1997 | Arnold |
| 6,764,850 B2 | 7/2004 | Maxwell et al. |
| 6,969,606 B2 | 11/2005 | Minton |
| 6,969,607 B2 | 11/2005 | Minton |
| 7,452,711 B2 | 11/2008 | Daykin |
| 2006/0240549 A1 | 10/2006 | Minton |

*Primary Examiner* — William H Beisner
*Assistant Examiner* — Michael Hobbs
(74) *Attorney, Agent, or Firm* — Chernoff, Vilhauer, McClung & Stenzel

(57) ABSTRACT

A lockable cell growth chamber is disclosed wherein the lid and base of the dish are provided with at least two pairs of locking and anti-locking members, the locking and antilocking functions being activated by application of rotational torque.

14 Claims, 4 Drawing Sheets

LOCKABLE CELL GROWTH CHAMBER WITH ANTILOCKING FEATURE

BACKGROUND OF THE INVENTION

The use of Petri dishes for growing colonies of microorganisms such as bacteria or fungi is well known. A Petri dish typically comprises an open dish for holding microorganism growth medium and an overlapping cover that isolates the growth medium and microorganisms from the external environment. A so-called mono plate is a slightly smaller version of a Petri dish that is used in large numbers in non-clinical settings such as food and pharma manufacturing, biotech labs and water testing.

Petri dish covers may be loosely fitting so that the seal on the dish arises simply from the weight of the cover bearing upon the cylindrical side walls of the dish. Petri dish covers may also be tightly securable to and detachable from the dish, which prevents opening of the Petri dish when it is accidentally bumped or knocked over. One such Petri dish design is disclosed in U.S. Pat. Nos. 3,769,936 and 5,854,065 wherein the cover may be secured to the dish by ribs or lugs in the side walls of the cover that resiliently contact the side walls of the dish so as to form a compression fit. However, this design has the inherent drawback that the compression fit is often either too tight to allow ready disengagement between the cover and dish or too loose, which can lead to accidental spillage or contamination when handling the Petri dish.

Mono plates are typically fabricated from polymeric material in mass quantities at a sufficiently low cost as to be disposable after a single use. The dish portion of the mono plate is pre-loaded with growth medium under sterile conditions and packaged for shipment to the end user.

There is an ongoing need in the art for a lockable cell growth chamber that does not lock except upon application of a specific intentionally applied force, and that, once locked, provides a locking engagement between the cover and the dish, and which may be readily disengaged from the locking engagement. These needs are met by the present invention, which is summarized and described in detail below.

BRIEF SUMMARY OF THE INVENTION

The present invention comprises a lockable cell growth chamber that may be in the form of a Petri dish or a mono plate wherein the cover and dish components are prevented from premature or accidental locking engagement with each other so as to permit rapid pre-loading with growth medium, yet are readily lockable and unlockable from each other.

The foregoing and other objectives, features, and advantages of the invention will be more readily understood upon consideration of the following detailed description of the invention taken in conjunction with the accompanying drawings.

DETAILED DESCRIPTION OF PREFERRED EMBODIMENTS

Figure 1:
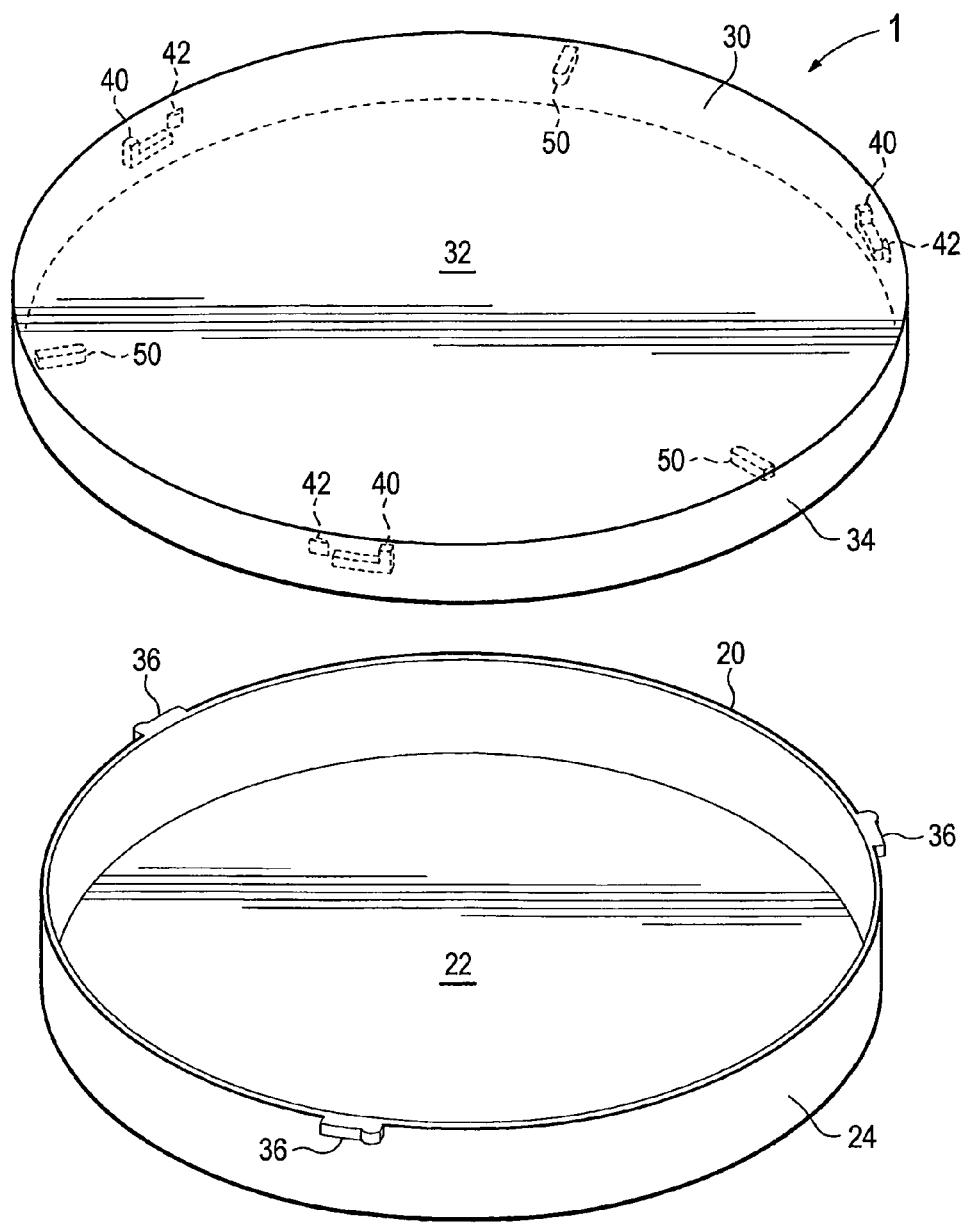
FIG. 1 is an exploded perspective view of exemplary embodiment of the lockable cell growth chamber of the invention.
Figure 2:
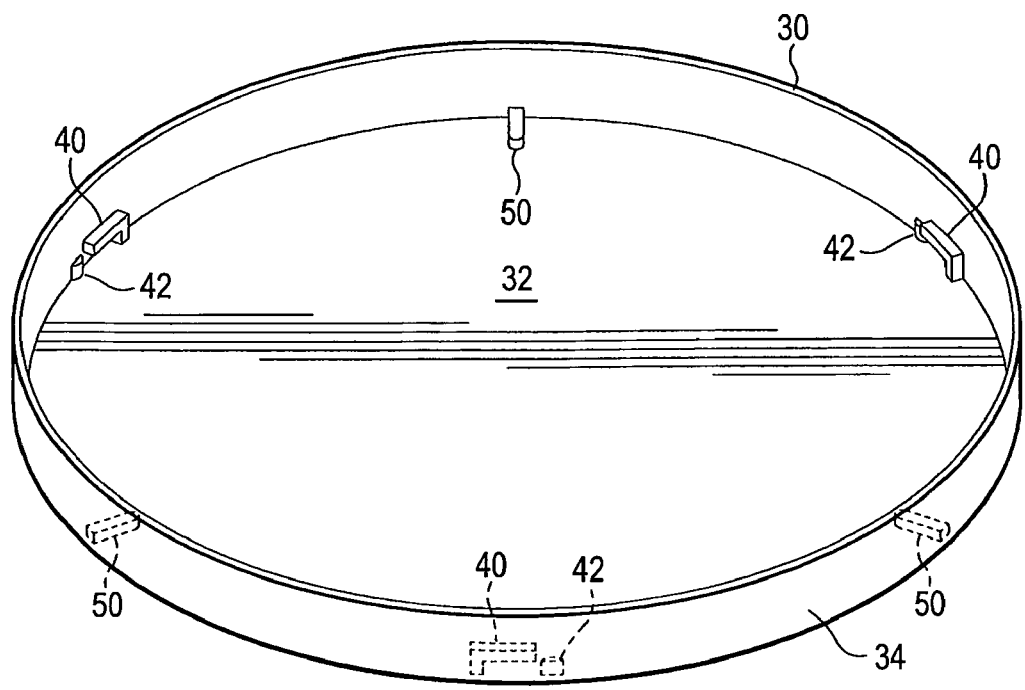
FIG. 2 is a perspective view of the underside of the lid of the cell growth chamber of FIG. 1 showing one of the two locking members.
Figure 3:
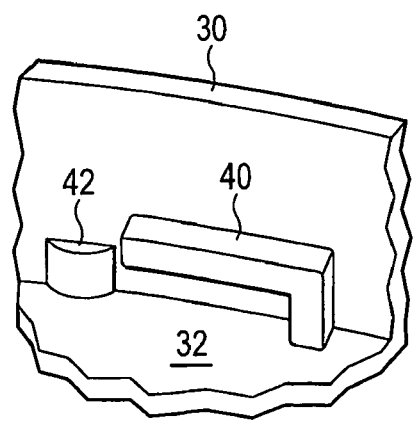
FIG. 3 is a perspective view of the locking member shown in FIG. 2.
Figure 4:
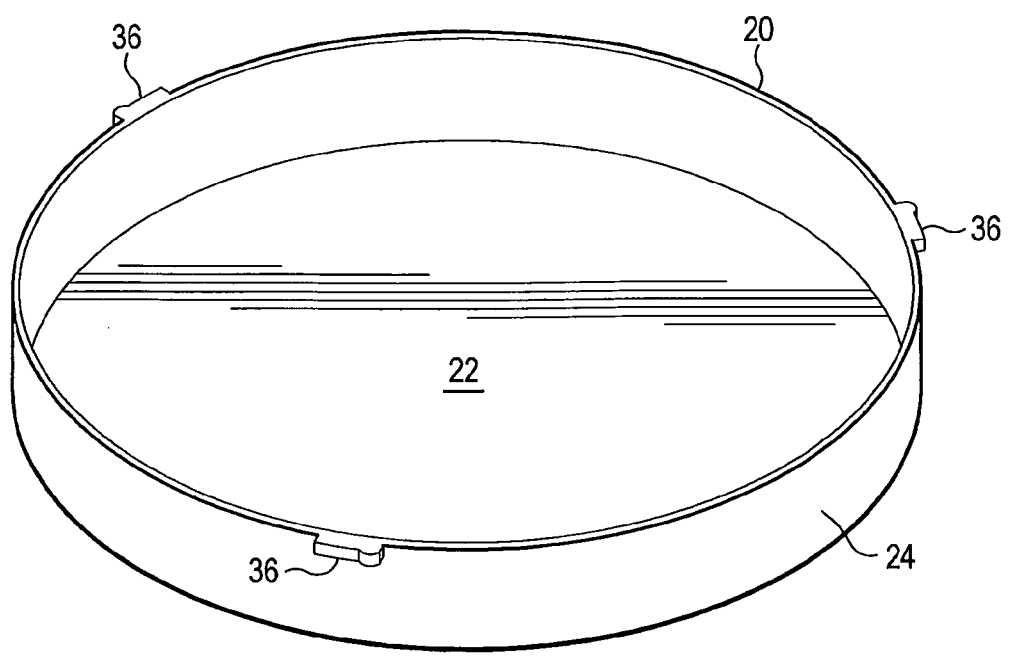
FIG. 4 is a perspective view of the dish or base portion of the cell growth chamber of FIG. 1 showing the other of the two locking members.
Figure 5:
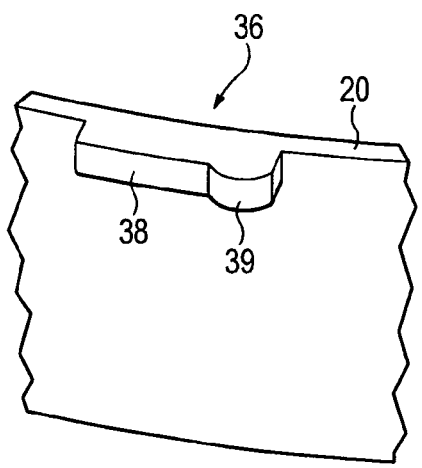
FIG. 5 is a partial perspective view of the locking member shown in FIG. 4.

Referring to the drawings, wherein the same numerals refer to like elements, there is shown in FIGS. 1-7 a cell growth chamber 1 comprising a circular dish 20, dish 20 consisting of a flat bottom plate 22 and a bottom cylindrical sidewall 24. The cell growth chamber further comprises a circular lid 30, consisting of a lid top plate 32 and a top cylindrical side wall 34. Lid 30 is preferably transparent so as to permit viewing of any microorganism growth.

Dish 20 and lid 30 are provided with locking means for securing the base and lid in locking engagement. The locking means comprises at least two pairs of locking members radially spaced apart from each other, preferably equidistantly, and more preferably at 120° relative to each other, wherein each pair of locking members comprises docking and tab members adapted to slidably and compressionably register with each other. More specifically, docking member 36 is preferably integral with bottom cylindrical side wall 24 of dish 20 and consists of a radial tab 38 having a raised tab boss 39, best seen in FIGS. 4-5. The inside of top cylindrical side wall 34 is provided with an L-shaped receiving member 40 oriented so as to be in registry with radial tab 38 and tab boss 39 of docking member 36 when dish 20 and lid 30 are in the locked position.

A blocking boss 42 is proximal to the open end of L-shaped receiving member 40, and is sized an shaped so as to have two functions: (1) it blocks entry of docking member 36 into L-shaped receiving member 40 except upon application of rotational torque to dish 20 and/or lid 30; and (2) once docking member 36 is fully engaged and in registry with L-shaped receiving member 40, it blocks disengagement except upon application of rotational torque in the opposite direction. This dual function is preferably accomplished by sizing blocking boss 42 slightly smaller in its inwardly radial direction than tab boss 39 in its outwardly radial direction, and making both blocking boss 42 and tab boss 39 from a resilient material such as a polymer, so that when the two elements 39 and 42 engage, each has a degree of yield or "give" when a rotational torqueing force is applied to dish 20 and/or lid 30, thereby allowing the two elements to pass over and by each other. Conversely, absent the application of such a rotational torqueing force, blocking boss 42 does not allow tab boss 39 to pass, thereby either preventing locking engagement of the dish and lid, or preventing disengagement once the dish and lid are locked together. Although docking member 36 and receiving member 40 with blocking boss 42 are preferably integral with dish 20 and lid 30, respectively, it should be understood that this arrangement could be reversed and still yield the desired locking means of the invention.

Lid top plate 32 may optionally be provided with radially inwardly projecting spacers 50 preferably spaced at approximately 120° relative to each other that create a small gap between dish 20 and lid 30 so as to permit air circulation. In the event the chamber is to be used in anaerobic applications, such spacers may be omitted.

Preferably all parts of the cell growth chamber are fabricated from a polymeric material having a slight degree of resiliency. A preferable polymeric material is polystyrene.

Figure 6:
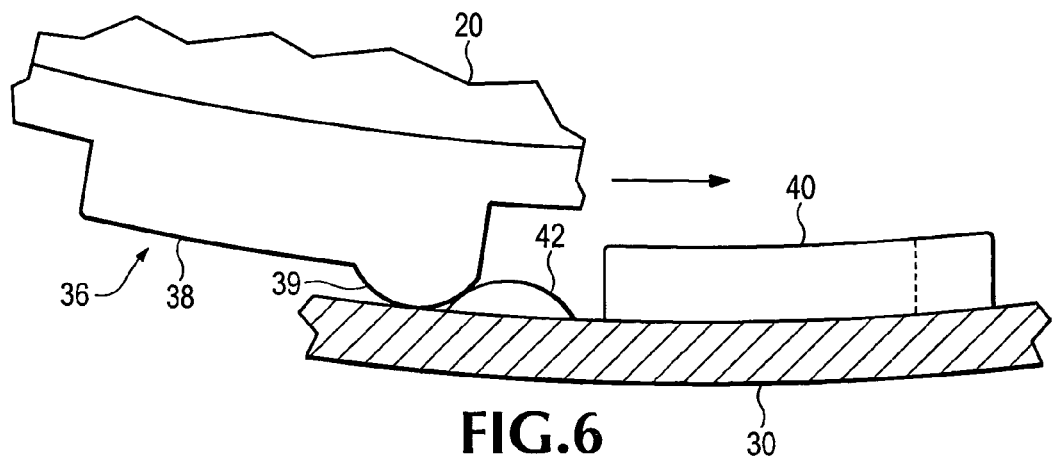
FIG. 6 is a cutaway view of the two locking members immediately prior to locking engagement illustrating how the boss of the locking member shown in FIG. 4 blocks locking engagement.
Figure 7:
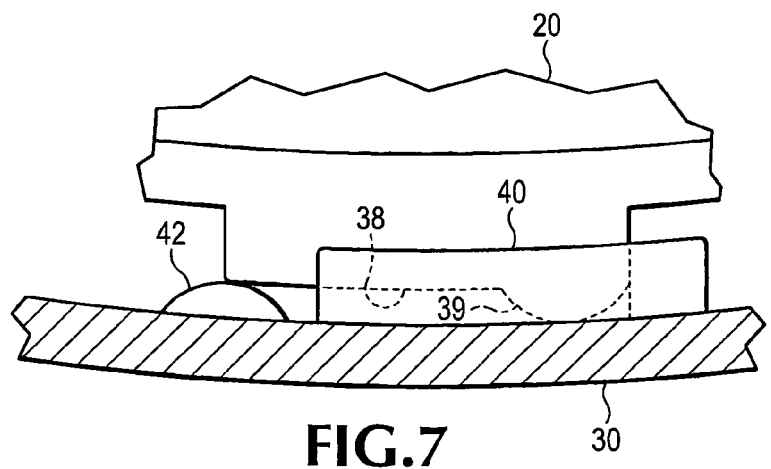
FIG. 7 is a cutaway view of the two locking members after locking engagement.

To engage the locking arrangement, lid 30 is placed over dish 20 so that tab bosses 39 of radial tabs 38 are proximate to blocking bosses 42, best seen in FIG. 6, then dish 20 is rotated relative to lid 30 (shown by the directional arrow in FIG. 6), or vice-versa, until tab bosses 39 engage blocking bosses 42. Rotation is continued and, because all parts of the cell growth chamber are made of polymer having a degree of resiliency, during the locking step, top cylindrical side wall 34, bottom cylindrical side wall 24, tab bosses 39 and blocking bosses 42 all distort slightly, then return to their original configuration as radial tabs 38 snap into registry with L-shaped receiving member 40, shown in FIG. 7. The closed ends of receiving members 40 prevent radial tabs 38 from further radial movement in the event excessive torqueing force is applied. Once dish 20 and lid 30 are in locking engagement, accidental removal of the lid from the base is prevented.

It is often advantageous to pre-load dish 20 with a growth medium such as agar or a gel containing microorganism-specific nutrients or indicators, then assemble the base and lid components, seal them in sterile packaging and ship them to the laboratory or other end user. Such pre-loading and pre-packaging is typically conducted on an automated basis, assembly-line style, with the lids rapidly being removed and replaced on the dishes by a mechanical arm immediately before and after the agar or gel pour. For speed and efficiency, it is best that, immediately before and after the loading, the lid not enter into locking engagement with the dish as this tends to interfere with and slow down the automated pre-loading process. As detailed above, the anti-locking aspect of the invention is particularly effective at preventing premature locking engagement between dish 20 and lid 30 on such a pre-loading assembly line.

The cell growth chamber of the invention containing growth medium is preferably manufactured in an unlocked arrangement and is packaged for shipment to the end user in gas-impermeable sterile packaging.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

The invention claimed is:

1. A lockable cell growth chamber comprising
    (a) a circular dish supported on a circular base, said dish having a bottom plate and a bottom cylindrical side wall, and
    (b) a circular lid having a top plate and a top cylindrical side wall, said lid sized so as to fit over the bottom cylindrical side wall of said dish
wherein said base and said lid are provided with anti-locking and locking means for both preventing locking engagement of said base and lid and for securing said base and lid in locking engagement, said anti-locking and locking means comprising at least two pairs of mateable members, each of said pairs of mateable members comprising (i) an L-shaped receiving member proximal to a blocking boss, and (ii) a radial tab sized and shaped so as to be stoppable by said blocking boss, yet slidably and compressionably engagable with said L-shaped docking member.

2. The cell growth chamber of claim 1 wherein said L-shaped receiving member is integral with the inside of said top plate and said top cylindrical side wall and said radial tab is integral with the outside of said bottom cylindrical side wall of said lid.

3. The cell growth chamber of claim 2 wherein said L-shaped receiving member has an open end to receive said radial tab and a closed end to form a stop for said radial tab.

4. The cell growth chamber of claim 3 wherein said blocking boss is proximal to said open end of said L-shaped receiving member.

5. The cell growth chamber of claim 4 wherein said blocking boss blocks engagement of said radial tab with said L-shaped receiving member except upon application of rotational torque to said dish and/or to said lid.

6. The cell growth chamber of claim 5 wherein said L-shaped receiving member and said radial tab are slidably engagable with each other by applying force to rotate said lid relative to said base.

7. The cell growth chamber of claim 6 wherein said L-shaped receiving member and said radial tab are slidably disengagable from each other by applying force to rotate said lid relative to said base.

8. The cell growth chamber of claim 7 wherein said radial tab is provided with a tab boss that is integral with said radial tab.

9. The cell growth chamber of claim 8 wherein the radial dimension of said blocking boss is slightly smaller than the radial dimension of said tab boss.

10. The cell growth chamber of claim 9 wherein the inside of said lid is provided with spacers.

11. The cell growth chamber of claim 10 wherein there are three of said spacers spaced at approximately 120° relative to each other.

12. The cell growth chamber of claim 1 wherein said lid is transparent.

13. The cell growth chamber of claim 1 wherein said dish contains microorganism growth medium.

14. The cell growth chamber of claim 13 packaged in sterile packaging.

* * * * *